US005681575A

United States Patent [19]
Burrell et al.

[11] Patent Number: 5,681,575
[45] Date of Patent: Oct. 28, 1997

[54] ANTI-MICROBIAL COATING FOR MEDICAL DEVICES

[75] Inventors: Robert Edward Burrell, Sherwood Park; Larry Roy Morris, Edmonton, both of Canada

[73] Assignee: Westaim Technologies Inc., Alberta, Canada

[21] Appl. No.: 57,968

[22] Filed: May 7, 1993

Related U.S. Application Data

[63] Continuation-in-part of Ser. No. 885,758, May 19, 1992, abandoned.

[51] Int. Cl.$^6$ ............................................. A61F 2/02
[52] U.S. Cl. .................................... 424/423; 424/423
[58] Field of Search ....................................... 424/423

[56] References Cited

U.S. PATENT DOCUMENTS

| | | | |
|---|---|---|---|
| 2,103,999 | 12/1937 | Muller et al. | 424/618 |
| 2,785,153 | 3/1957 | Locke et al. | 514/6 |
| 4,043,932 | 8/1977 | Fresenius et al. | 252/95 |
| 4,054,139 | 10/1977 | Crossley | 604/265 |
| 4,167,045 | 9/1979 | Sawyer | 427/2 |
| 4,325,776 | 4/1982 | Menzel | 117/8 |
| 4,341,569 | 7/1982 | Yaron et al. | 437/19 |
| 4,377,675 | 3/1983 | Daudt et al. | 528/25 |
| 4,404,233 | 9/1983 | Ikeda et al. | 427/35 |
| 4,411,041 | 10/1983 | Braga | 15/167 |
| 4,411,648 | 10/1983 | Davis et al. | 604/21 |
| 4,418,686 | 12/1983 | Child | 604/285 |
| 4,443,488 | 4/1984 | Little et al. | 204/157.44 |
| 4,476,590 | 10/1984 | Scales et al. | 623/18 |
| 4,483,688 | 11/1984 | Akiyama | 604/265 |
| 4,520,039 | 5/1985 | Ovshinsky | 427/457 |
| 4,528,208 | 7/1985 | Hivonen et al. | 427/35 |
| 4,543,275 | 9/1985 | Akashi et al. | 427/250 |
| 4,564,361 | 1/1986 | Akiyama | 604/265 |
| 4,569,673 | 2/1986 | Tesi | 604/20 |
| 4,590,031 | 5/1986 | Eichen et al. | 264/338 |
| 4,592,920 | 6/1986 | Murtfeldt | 427/2.3 |
| 4,603,152 | 7/1986 | Laurin et al. | 604/265 |
| 4,612,337 | 9/1986 | Fox, Jr. et al. | 514/38 |
| 4,615,705 | 10/1986 | Scales et al. | 424/426 |
| 4,642,104 | 2/1987 | Sakamoto et al. | 604/264 |
| 4,657,772 | 4/1987 | Kocak | 427/2.28 |
| 4,664,960 | 5/1987 | Ovshinsky | 428/98 |
| 4,670,292 | 6/1987 | Fujita et al. | 427/552 |
| 4,677,143 | 6/1987 | Laurin et al. | 424/618 |
| 4,683,149 | 7/1987 | Suzuki et al. | 427/38 |
| 4,693,760 | 9/1987 | Sioshansi | 427/524 |
| 4,716,083 | 12/1987 | Eicken et al. | 428/457 |
| 4,718,905 | 1/1988 | Freeman | 623/6 |
| 4,743,308 | 5/1988 | Sioshansi et al. | 148/239 |
| 4,743,493 | 5/1988 | Sioshansi et al. | 428/217 |
| 4,846,834 | 7/1989 | von Recum et al. | 623/11 |
| 4,849,223 | 7/1989 | Pratt et al. | 424/409 |
| 4,855,026 | 8/1989 | Sioshansi | 204/192.11 |
| 4,867,968 | 9/1989 | Allen | 514/39 |
| 4,886,505 | 12/1989 | Haynes et al. | 604/265 |
| 4,902,503 | 2/1990 | Umemura et al. | 514/6 |

(List continued on next page.)

FOREIGN PATENT DOCUMENTS

| | | |
|---|---|---|
| 1 106 718 | 8/1981 | Canada. |
| 2 033 107 | 6/1992 | Canada. |
| 0 206 024 | 12/1986 | European Pat. Off.. |
| 0 254 413 | 1/1988 | European Pat. Off.. |
| 0 415 206 A2 | 3/1991 | European Pat. Off.. |
| 0 488 269 | 6/1992 | European Pat. Off.. |
| 2 634 986 | 2/1990 | France. |
| 819 131 | 12/1948 | Germany. |
| 25 30 487 | 1/1977 | Germany. |
| 33 02 567 A1 | 7/1984 | Germany. |
| 38 30 359 A1 | 12/1989 | Germany. |
| 90 17 361.9 | 3/1991 | Germany. |
| 57-500588 | 4/1982 | Japan. |
| 60-21912 | 2/1985 | Japan. |
| 62-56018 | 4/1987 | Japan. |
| 2 073 024 | 10/1981 | United Kingdom. |
| 2 134 791 | 8/1984 | United Kingdom. |
| 2 134 791 A | 8/1984 | United Kingdom. |
| PCT/US92/08266 | 4/1993 | WIPO. |

OTHER PUBLICATIONS

H.E. Morton, "Pseudomonas," in *Antiseptics and Disinfectants*, 401–411 (S.S. Block, Lea, and Febiger ed. 1977).

N. Grier "Silver and Its Compounds," in *Antiseptics and Disinfectants*, 375–389, S.S. Block, Lea and Febiger ed. 1977).

E. Deitch et al., "Silver–Nylon: A New Antimicrobial Agent," Antimicrobial Agents and Chemotherapy, vol. 23 (3):356–359 (Mar. 1983).

P. MacKeen et al., "Silver–Coated Nylon Fiber as an Antibacterial Agent," Antimicrobial Agents and Chemotherapy, vol. 31 (1):93–99 (Jan. 1987).

A. Marino et al., "Electrical Augmentation of the Antimicrobial Activity of Silver–Nylon Fabrics," Journal of Biological Physics, vol. 12: 93–98 (1984).

M. Tanemura et al., "Growth of microprojections arising from sputter etching of Cu–Ag sandwich," J. Vac. Sci. Technol., vol. 4, (5): 2369–2372 (Sep./Oct. 1986).

(List continued on next page.)

*Primary Examiner*—Carlos A. Azpuru
*Attorney, Agent, or Firm*—Finnegan, Henderson, Farabow, Garrett & Dunner, L.L.P.

[57] ABSTRACT

Anti-microbial coatings and method of forming same on medical devices are provided. The coatings are formed by depositing a biocompatible metal by vapor deposition techniques to produce atomic disorder in the coating such that a sustained release of metal ions sufficient to produce an anti-microbial effect is achieved. Preferred deposition conditions to achieve atomic disorder include a lower than normal substrate temperature, and one or more of a higher than normal working gas pressure and a lower than normal angle of incidence of coating flux. Anti-microbial powders formed by mechanical working to produce atomic disorder are also provided. The invention extends to other metal coatings and powders similarly formed so as to provide enhanced solubility.

25 Claims, No Drawings

5,681,575
Page 2

U.S. PATENT DOCUMENTS

| | | | |
|---|---|---|---|
| 4,906,466 | 3/1990 | Edwards et al. | 424/78 |
| 4,923,450 | 5/1990 | Maeda et al. | 604/265 |
| 4,932,948 | 6/1990 | Kernes et al. | 604/349 |
| 4,933,178 | 6/1990 | Capelli | 424/403 |
| 4,944,961 | 7/1990 | Lu et al. | 427/531 |
| 4,952,419 | 8/1990 | De Leon et al. | 427/2 |
| 4,960,415 | 10/1990 | Reinmuller | 604/890.1 |
| 4,973,320 | 11/1990 | Brenner et al. | 604/265 |
| 5,005,518 | 4/1991 | Yamada | 118/716 |
| 5,019,096 | 5/1991 | Fox, Jr. et al. | 623/1 |
| 5,019,601 | 5/1991 | Allen | 514/39 |
| 5,045,318 | 9/1991 | Tengvall et al. | 424/422 |
| 5,047,385 | 9/1991 | Beasley et al. | 505/325 |
| 5,049,140 | 9/1991 | Brenner et al. | 604/266 |
| 5,055,169 | 10/1991 | Hock, Jr. et al. | 204/192.31 |
| 5,057,106 | 10/1991 | Kasevich et al. | 606/33 |
| 5,073,382 | 12/1991 | Antelman | 424/604 |
| 5,078,902 | 1/1992 | Antelman | 210/764 |
| 5,080,671 | 1/1992 | Oron et al. | 623/16 |
| 5,089,275 | 2/1992 | Antelman | 424/602 |
| 5,098,434 | 3/1992 | Serbousek | 606/73 |
| 5,098,582 | 3/1992 | Antelman | 210/759 |
| 5,108,399 | 4/1992 | Eitenmuller et al. | 606/77 |
| 5,123,924 | 6/1992 | Sioshansi et al. | 623/16 |
| 5,123,927 | 6/1992 | Duncan et al. | 623/20 |
| 5,133,757 | 7/1992 | Sioshansi et al. | 623/18 |
| 5,152,774 | 10/1992 | Schroeder | 428/457 |
| 5,152,783 | 10/1992 | Suzuki et al. | 623/1 |
| 5,152,993 | 10/1992 | Bjursten et al. | 424/422 |
| 5,180,585 | 1/1993 | Jacobson et al. | 424/405 |
| 5,207,706 | 5/1993 | Menaker | 623/12 |
| 5,211,855 | 5/1993 | Antelman | 210/758 |
| 5,223,149 | 6/1993 | Antelman | 210/764 |
| 5,242,706 | 9/1993 | Cotell et al. | 427/2 |
| 5,322,520 | 6/1994 | Milder | 604/265 |
| 5,405,644 | 4/1995 | Ohsumi et al. | 427/2.31 |
| 5,427,631 | 6/1995 | Johansson et al. | 148/23.8 |
| 5,454,886 | 10/1995 | Burrell et al. | 148/565 |
| 5,468,562 | 11/1995 | Farivar et al. | 428/457 |
| 5,474,797 | 12/1995 | Sioshansi et al. | 427/224 |
| 5,520,664 | 5/1996 | Bricault, Jr. et al. | 604/265 |

OTHER PUBLICATIONS

R. Bunshah, "Deposition Technologies: An Overview," in *Deposition Technologies for Films and Coatings*, Noyes Publications, N.J., 1–18 (1982).

J. Thornton, "Influence of apparatus geometry and deposition conditions on the structure and topography of thick sputtered coatings," J. Vac. Sci. Technol., Vol. 11, (4):666–670 (Jul./Aug. 1974).

R.P. Andres et al., "Research opportunities on clusters and cluster–assembled materials—A Department of Energy, Council on Materials Science Panel Report," J. Mater. Res., vol. 4, (3): 704–736 (May/Jun. 1989).

J. Nickel et al., "Antibiotic Resistance of Pseudomonus aeruginosa Colonizing a Urinary Catheter in Vivo," Eur. J. Clin. Microbiol, vol. 4 (2):213–218 (Apr. 1985).

Product Brochures; SPI–ARGENT.

P. Sioshansi, "Surface Coatings by Ion Beam Assisted Deposition," presented at Thin Films '91, San Diego, Calif., Sep. 26 & 27, 1991.

Letter and enclosures dated Dec. 16, 1991, from John E. Barry (Spire Corporation) to Applicant, Dr. Burrell.

Announcement by Spire Corp. in *New Coatings and Surfaces*, Sep. 1991.

S. Barranco et al., "In Vitro Effect of Weak Direct Current on Staphylococcus Aureus," Clinical Orthopaedics and Related Research, No. 100, 250–255 (May 1974).

J. Spadaro et al., "Antibacterial Effects of Silver Electrodes with Week Direct Current," Antimicrobial Agents and Chemotherapy, vol. 6 (5):637–642 (Nov. 1974).

J. Spadaro et al., "Some Specific Cellular Effects of Electrically Injected Silver and Gold Ions," Bioelectrochem. and Bioenergetics, No. 3, 49–57 (1976).

T. Berger et al., "Electrically Generated Silver Ions: Quantitative Effects on Bacterial and Mammalian Cells," Antimicrobial Agents and Chemotherapy, 357–358 (Feb. 1976).

T. Berger et al., "Antifungal Properties of Electrically Generated Metallic Ions," Antimicrobial Agents and Chemotherapy, vol. 10 (5): 856–860 (Nov. 1976).

J. Spadaro, "Antibacterial Effects of Silver Electrodes," Eng. in Med. & Biol. Soc., 215–218 (1981).

D. Webster et al., "Silver Anode Treatment of Chronic Osteomyelitis," Clinical Orthopaedics and Related Research, No. 161, 105–114 (Nov./Dec. 1981).

C. Davis et al., "Iontophoretic Killing of *Escherichia* coli in Static Fluid and in a Model Catheter System," Journal of Clinical Microbiology, vol. 15 (5): 891–894 (May 1982).

J. Spadaro et al., "Antibacterial Fixation Pins With Silver: Animal Models," J. Biol. Phys., No. 12 (1984).

A. Marino et al., "Electrochemical Properties of Silver–Nylon Fabrics," J. Electrochem. Soc., vol. 132 (1):68–72 (Jan. 1985).

J. Spadaro, "Bone Formation and Bacterial Inhibition with Silver and Other Electrodes," Reconstr. Surg. Traumat., vol. 19, 40–50 (1985).

A. Falcone et al., "Inhibitory Effects of Electrically Activated Silver Material on Cutaneous Wound Bacteria," Plastic and Reconstructuve Surgery, 455–459 (Mar. 1986).

J. Spadaro et al., "Bacterial inhibition by electrical activation of percutaneous silver implants," Journal of Biomedical Materials Research, vol. 20, 565–577 (1986).

R.E. Hall et al., "Inhibitory and Cidal Antimicrobial Actions of Electrically Generated Silver Ions," J. Oral Maxillofac. Surg., No. 45, 779–784 (1987).

C.P. Davis et al., "Effects of Microamperage, Medium, and Bacterial Concentration of Iontophoretic Killing of Bacteria in Fluid," Antimicrobial Agents and Chemotherapy, vol. 33 (4): 442–447 (Apr. 1989).

R. Kirchheim et al., "Free Energy of Active Atoms in Grain Boundaries of Nanocrystalline Copper, Nickel and Palladium," Nanostructed Materials, vol. 1, 167–172 (1992).

E. Deitch et al., "Silver Nylon Cloth: In vitro and in vivo Evaluation of Antimicrobial Activity," Journal of Trauma, vol. 27 (3): 301–304 (1987).

J. Thornton, "Coating Deposition by Sputtering," in *Deposition Technologies For Films and Coatings*, Noyes Publications, N.J. 170–237 (1982).

M. Lardon et al., "Influence of the substrate temperature and the discharge voltage on the structure of titanium films produced by ion–plating," Vacuum, vol. 30 (7):255–260 (1980).

F. Froes et al., "Nanocrystalline Metals for Structural Applications", JOM, vol. 41 (6):12–17 (Jun. 1989).

W. Schlump et al., "Nanocrystalline materials by mechanical alloying," Technische Mitteilungen Krupp, No. 2, 69–76 (Nov. 1989).

Gleiter, H., 1992. "Materials With Ultrafine Microstructures: Retrospective and Perspectives" NanoStructured Materials, vol. 1, pp. 1–19.

Birringer, R., et al., 1986. "Nanocrystalline Materials—A First Report" Grain Boudary Structure and Related Phenomena Proceedings of JIMIS–4 (1986). Supplement to Transactions of the Japan Institute of Metals.

Spadaro, J.A., et al, 1979. "Silver Polymethyl Methacrylate Antibacterial Bone Cement" Clinical Orthopaedics and Related Research, No. 143, Sep. 1979, pp. 266–270.

Becker, R.O., et al., 1978. "Treatment of Orthopaedic Infections with Electrically Generated Silver Ions" The Journal of Bone and Joint Surgery, vol. 60–A, No. 7, Oct. 1978, pp. 871–881.

Research & Development Magazine, Oct. 1993, Consumer Products "SILDATE".

Colmano, G., et al. 1980. "Activation of Antibacterial Silver Coatings on Surgical Implants by Direct Current: Preliminary Studies in Rabbits", Am.J.Vet.Res., vol. 41, No. 6, 1980, pp. 964–966.

Spadaro, J.A., et al. 1983. "Direct Current Activation of Bacteriostatic Silver Electrodes—1983 abstract—Transactions of the Bioelectric Repair and Growth Society", vol. 3, pp. 37.

Spadaro, J.A., et al. 1981. "Electrical Activation of Silver Bacteriostasis—Transactions of Society For Biomaterials", vol. 4, p. 70, 1981.—presented at the 7th Annual Meeting Society for Biomaterials, Troy New York, May 29, 1981.

ANTI-MICROBIAL COATING FOR MEDICAL DEVICES

CROSS-REFERENCE TO RELATED APPLICATION

This application is a continuation-in-part of application Ser. No. 07/885,758, filed May 19, 1992, now abandoned, the entire disclosure of which is hereby relied upon.

FIELD OF THE INVENTION

This invention relates to methods for preparing modified materials such as metal coatings or powders in a form such that metal species are released on a sustainable basis at an enhanced rate. In a particular aspect, the invention relates to methods of forming anti-microbial coatings and powders of biocompatible metals which provide a sustained release of anti-microbial metal species when in contact with body fluids or body tissues.

BACKGROUND OF THE INVENTION

The need for an effective anti-microbial coating is well established in the medical community. Physicians and surgeons using medical devices and appliances ranging from orthopaedic pins, plates and implants through to wound dressings and urinary catheters must constantly guard against infection. An inexpensive anti-microbial coating also finds application in medical devices used in consumer healthcare and personal hygiene products as well as in biomedical/biotechnical laboratory equipment. The term "medical device", as used herein and in the claims is meant to extend to all such products.

The anti-microbial effects of metallic ions such as Ag, Au, Pt, Pd, Ir (i.e. the noble metals), Cu, Sn, Sb, Bi and Zn are known (see Morton, H. E., Pseudomonas in Disinfection, Sterilization and Preservation, ed. S. S. Block, Lea and Febiger, 1977 and Grier, N., Silver and Its Compounds in Disinfection, Sterilization and Preservation, ed. S. S. Block, Lea and Febiger, 1977). Of the metallic ions with anti-microbial properties, silver is perhaps the best known due to its unusually good bioactivity at low concentrations. This phenomena is termed oligodynamic action. In modern medical practice both inorganic and organic soluble salts of silver are used to prevent and treat microbial infections. While these compounds are effective as soluble salts, they do not provide prolonged protection due to loss through removal or complexation of the free silver ions. They must be reapplied at frequent intervals to overcome this problem. Reapplication is not always practical, especially where an in-dwelling or implanted medical device is involved.

Attempts have been make to slow the release of silver ions during treatment by creating silver containing complexes which have a lower level of solubility. For example, U.S. Pat. No. 2,785,153 discloses colloidal silver protein for this purpose. Such compounds are usually formulated as creams. These compounds have not found wide applicability in the medical area due to their limited efficacy. The silver ion release rate is very slow. Furthermore, coatings from such compounds have been limited due to adhesion, abrasion resistance and shelf life problems.

The use of silver metal coatings for anti-microbial purposes has been suggested. For instance, see Deitch et at., Antimicrobial Agents and Chemotherapy, Vol. 23(3), 1983, pp. 356–359 and Mackeen et at., Antimicrobial Agents and Chemotherapy, Vol. 31(1), 1987, pp. 93–99. However, it is generally accepted that such coatings alone do not provide the required level of efficacy, since diffusion of silver ions from the metallic surface is negligible.

A silver metal coating is produced by Spire Corporation, U.S.A. under the trade mark SPI-ARGENT. The coating is formed by an ion-beam assisted deposition (IBAD) coating process. The infection resistant coating is stated to be non-leaching in aqueous solutions as demonstrated by zone of inhibition tests, thus enforcing the belief that silver metal surfaces do not release anti-microbial amounts of silver ions.

Given the failure of metallic silver coatings to generate the required anti-microbial efficacy, other researchers have tried novel activation processes. One technique is to use electrical activation of metallic silver implants (see Marino et al., Journal of Biological Physics, Vol. 12, 1984, pp. 93–98). Electrical stimulation of metallic silver is not always practical, especially for mobile patients. Attempts to overcome this problem include developing in situ electrical currents through galvanic action. Metal bands or layers of different metals are deposited on a device as thin film coatings. A galvanic cell is created when two metals in contact with each other are placed in an electrically conducting fluid. One metal layer acts as an anode, which dissolves into the electrolyte. The second metal acts as a cathode to drive the electrochemical cell. For example, in the case of alternating layers of Cu and Ag, the Cu is the anode, releasing $Cu^+$ ions into the electrolyte. The more noble of the metals, Ag, acts as the cathode, which does not ionize and does not go into solution to any large extent. An exemplary device of this nature is described in U.S. Pat. No. 4,886,505 issued Dec. 12, 1989, to Haynes et al. The patent discloses sputtered coatings of two or more different metals with a switch affixed to one of the metals such that, when the switch is closed, metal ion release is achieved.

Previous work has shown that a film composed of thin laminates of alternating, different metals such as silver and copper can be made to dissolve if the surface is first etched. In this instance, the etching process creates a highly textured surface (see M. Tanemura and F. Okuyama, J. Vac. Sci. Technol., 5, 1986, pp 2369–2372). However, the process of making such multilaminated films is time consuming and expensive.

Electrical activation of metallic coatings has not presented a suitable solution to the problem. It should be noted that galvanic action will occur only when an electrolyte is present and if an electrical connection between the two metals of the galvanic couple exists. Since galvanic corrosion occurs primarily at the metallic interface between the two metals, electrical contact is not sustained. Thus a continuous release of metal ions over an extended period of time is not probable. Also, galvanic action to release a metal such as silver is difficult to achieve. As indicated above, the metal ions exhibiting the greatest anti-microbial effect are the noble metals, such as Ag, Au, Pt and Pd. There are few metals more noble than these to serve as cathode materials so as to drive the release of a noble metal such as Ag at the anode.

A second approach to activating the silver metal surface is to use heat or chemicals. U.S. Pat. Nos. 4,476,590 and 4,615,705, issued to Scales et al. on Oct. 16, 1984 and Oct. 7, 1986, respectively, disclose methods of activating silver surface coatings on endoprosthetic implants to render them bioerodible by heating at greater than 180° C. or by contacting with hydrogen peroxide. Such treatments are limited in terms of the substrate/devices which can be coated and activated.

There is still a need for an efficacious, inexpensive anti-microbial material having the following properties:

sustained release of an anti-microbial agent at therapeutically active levels;
applicable to a wide variety of devices and materials;
useful shelf life; and
low mammalian toxicity.

Metal coatings are typically produced as thin films by vapour deposition techniques such as sputtering. Thin films of metals, alloys, semiconductors and ceramics are widely used in the production of electronic components. These and other end uses require the thin rims to be produced as dense, crystalline structures with minimal defects. The films are often annealed after deposition to enhance grain growth and recrystallization and produce stable properties. Techniques to deposit metal films are reviewed by R. F. Bunshah et al., "Deposition Technologies for Films and Coatings", Noyes Publications, N. J., 1982 and by J. A. Thornton, "Influence of Apparatus Geometry and Deposition Conditions on the Structure and Topography of Thick Sputtered Coatings", J. Vac. Sci. Technol., 11(4), 666–670, 1974.

U.S. Pat. No. 4,325,776, issued Apr. 20, 1982 to Menzel discloses a process for producing coarse or single crystal metal films from certain metals for use in integrated circuits. The metal fill is formed by depositing on a cooled substrate (below −90° C.) such that the metal layer is in an amorphous phase. The metal layer is then annealed by heating the substrate up to about room temperature. The end product is stated to have large grain diameter and great homogeneity, permitting higher current densities without electromigration failures.

SUMMARY OF THE INVENTION

The inventors set out to develop an antimicrobial metal coating. They discovered that, contrary to previous belief, it is possible to form metal coatings from an antimicrobial metal material by creating atomic disorder in the materials by vapour deposition under conditions which limit diffusion, that is which "freeze-in" the atomic disorder. The antimicrobial coatings so produced were found to provide sustained release of anti-microbial metal species into solution so as to produce an anti-microbial effect.

This basic discovery linking "atomic disorder" to enhanced solubility has broad application. The inventors have demonstrated that atomic disorder so as to produce solubility can be created in other material forms, such as metal powders. The invention also has application beyond anti-microbial metals, encompassing any metal, metal alloy, or metal compound, including semiconductor or ceramic materials, from which sustained release of metal species into solution is desired. For instance, materials having enhanced or controlled metal dissolution find application in sensors, switches, fuses, electrodes, and batteries.

The term "atomic disorder" as used herein includes high concentrations of: point defects in a crystal lattice, vacancies, line defects such as dislocations, interstitial atoms, amorphous regions, grain and sub grain boundaries and the like relative to its normal ordered crystalline state. Atomic disorder leads to irregularities in surface topography and inhomogenieties in the structure on a nanometer scale.

By the term "normal ordered crystalline state" as used herein is meant the crystallinity normally found in bulk metal materials, alloys or compounds formed as cast, wrought or plated metal products. Such materials contain only low concentrations of such atomic defects as vacancies, grain boundaries and dislocations.

The term "diffusion" as used herein implies diffusion of atoms and/or molecules on the surface or in the matrix of the material being formed.

The terms "metal" or "metals" as used herein are meant to include one or more metals whether in the form of substantially pure metals, alloys or compounds such as oxides, nitrides, borides, sulphides, halides or hydrides.

The invention, in a broad aspect extends to a method of forming a modified material containing one or more metals. The method comprises creating atomic disorder in the material under conditions which limit diffusion such that sufficient atomic disorder is retained in the material to provide release, preferably on a sustainable basis, of atoms, ions, molecules or clusters of at least one of the metals into a solvent for the material. Clusters are known to be small groups of atoms, ions or the like, as described by R. P. Andres et at., "Research Opportunities on Clusters and Cluster-Assembled Materials", J. Mater. Res. Vol. 4, No. 3, 1989, P. 704.

Specific preferred embodiments of the invention demonstrate that atomic disorder may be created in metal powders or foils by cold working, and in metal coatings by depositing by vapour deposition at low substrate temperatures.

In another broad aspect, the invention provides a modified material comprising one or more metals in a form characterized by sufficient atomic disorder such that the material, in contact with a solvent for the material, releases atoms, ions, molecules or clusters containing at least one metal, preferably on a sustainable basis, at an enhanced rate relative to its normal ordered crystalline state.

In preferred embodiments of the invention, the modified material is a metal powder which has been mechanically worked or compressed, under cold working conditions, to create and retain atomic disorder.

The term "metal powder" as used herein is meant to include metal particles of a broad particle size, ranging from nanocrystalline powders to flakes.

The term "cold working" as used herein indicates that the material has been mechanically worked such as by milling, grinding, hammering, mortar and pestle or compressing, at temperatures lower than the recrystallization temperature of the material. This ensures that atomic disorder imparted through working is retained in the material.

In another preferred embodiment, the modified material is a metal coating formed on a substrate by vapour deposition techniques such as vacuum evaporation, sputtering, magnetron sputtering or ion plating. The material is formed under conditions which limit diffusion during deposition and which limit annealing or recrystallization following deposition. The deposition conditions preferably used to produce atomic disorder in the coatings are outside the normal range of operating conditions used to produce defect free, dense, smooth films. Such normal practices are well known (see for example R. F. Bunshah et al., supra). Preferably the deposition is conducted at low substrate temperatures such that the ratio of the substrate to the melting point of the metal or metal compound being deposited (T/Tm) is maintained at less than about 0.5, more preferably at less than about 0.35, and most preferably at less than 0.30. In this ratio, the temperatures are in degrees Kelvin. The preferred ratio will vary from metal to metal and increases with alloy or impurity content. Other preferred deposition conditions to create atomic disorder include one or more of a higher than normal working gas pressure, a lower than normal angle of incidence of the coating flux and a higher than normal coating flux.

The temperature of deposition or cold working is not so low that substantial annealing or recrystallization will take place when the material is brought to room temperature or its intended temperature for use (ex. body temperature for anti-microbial materials). If the temperature differential between deposition and temperature of use (ΔT) is too great, annealing results, removing atomic disorder. This ΔT will vary from metal to metal and with the deposition technique used. For example, with respect to silver, substrate temperatures of −20° to 200° C. are preferred during physical vapour deposition.

Normal or ambient working gas pressure for depositing the usually required dense, smooth, defect free metal films vary according to the method of physical vapour deposition being used. In general, for sputtering, the normal working gas pressure is less 75 mT (milliTorr), for magnetron sputtering, less than 10 mT, amd for ion-plating less than 200 mT. Normal ambient gas pressures vary for vacuum evaporation processes vary as follows: for e-beam or arc evaporation, from 0.001 to 0.01 mT; for gas scattering evaporation (pressure plating) and reactive are evaporation, up to 200 mT, but typically less than 20 mT. Thus, in accordance with the method of the present invention, in addition to using low substrate temperatures to achieve atomic disorder, working (or ambient) gas pressures higher than these normal values may be used to increase the level of atomic disorder in the coating.

Another condition discovered to have an effect on the level of atomic disorder in the coatings of the present invention is the angle of incidence of the coating flux during deposition. Normally to achieve dense, smooth coatings, this angle is maintained at about 900°±15°. In accordance with the present invention, in addition to using low substrate temperatures during deposition to achieve atomic disorder, angles of incidence lower than about 75° may be used to increase the level of atomic disorder in the coating.

Yet another process parameter having an effect on the level of atomic disorder is the atom flux to the surface being coated. High deposition rates tend to increase atomic disorder, however, high deposition rates also tend to increase the coating temperature. Thus, there is an optimum deposition rate that depends on the deposition technique, the coating material and other process parameters.

To provide an anti-microbial material, the metals used in the coating or powder are those which have an anti-microbial effect, but which are biocompatible (non-toxic for the intended utility). Preferred metals include Ag, Au, Pt, Pd, Ir (i.e. the noble metals), Sn, Cu, Sb, Bi, and Zn, compounds of these metals or alloys containing one more of these metals. Such metals are hereinafter referred to as "anti-microbial metals"). Most preferred is Ag or its alloys and compounds. Anti-microbial materials in accordance with this invention preferably are formed with sufficient atomic disorder that atoms, ions, molecules or clusters of the anti-microbial material are released into an alcohol or water based electrolyte on a sustainable basis. The terms "sustainable basis" is used herein to differentiate, on the one hand from the release obtained from bull metals, which release metal ions and the like at a rate and concentration which is too low to achieve an anti-microbial effect, and on the other hand from the release obtained from highly soluble salts such as silver nitrate, which release silver ions virtually instantly in contact with an alcohol or water based electrolyte. In contrast, the anti-microbial materials of the present invention release atoms, ions, molecules or clusters of the anti-microbial metal at a sufficient rate and concentration, over a sufficient time period to provide a useful anti-microbial effect.

The term "anti-microbial effect" as used herein means that atoms, ions, molecules or clusters of the anti-microbial metal are released into the electrolyte which the material contacts in concentrations sufficient to inhibit bacterial growth in the vicinity of the material. The most common method of measuring anti-microbial effect is by measuring the zone of inhibition (ZOI) created when the material is placed on a bacterial lawn. A relatively small or no ZOI (ex. less than 1 mm) indicates a non-useful anti-microbial effect, while a larger ZOI (ex. greater than 5 mm) indicates a highly useful anti-microbial effect. One procedure for a ZOI test is set out in the Examples which follow.

The invention extends to devices such as medical devices formed from, incorporating, carrying or coated with the anti-microbial powders or coatings. The anti-microbial coating may be directly deposited by vapour deposition onto such medical devices as catheters, sutures, implants, burn dressings and the like. An adhesion layer, such as tantalum, may be applied between the device and the anti-microbial coating. Adhesion may also be enhanced by methods known in the art, for example etching the substrate or forming a mixed interface between the substrate and the coating by simultaneous sputtering and etching. Anti-microbial powders may be incorporated into creams, polymers, ceramics, paints, or other matrices, by techniques well known in the art.

In a further broad aspect of the invention, modified materials are prepared as composite metal coatings containing atomic disorder. In this case, the coating of the one or more metals or compounds to be released into solution constitutes a matrix containing atoms or molecules of a different material. The presence of different atoms or molecules results in atomic disorder in the metal matrix, for instance due to different sized atoms. The different atoms or molecules may be one or more second metals, metal alloys or metal compounds which are co⁻ or sequentially deposited with the fast metal or metals to be released. Alternatively the different atoms or molecules may be absorbed or trapped from the working gas atmosphere during reactive vapour deposition. The degree of atomic disorder, and thus solubility, achieved by the inclusion of the different atoms or molecules varies, depending on the materials. In order to retain and enhance the atomic disorder in the composite material, one or more of the above-described vapour deposition conditions, namely low substrate temperature, high working gas pressure, low angle of incidence and high coating flux, may be used in combination with the inclusion of different atoms or molecules.

Preferred composite materials for anti-microbial purposes are formed by including atoms or molecules containing oxygen, nitrogen, hydrogen, boron, sulphur or halogens in the working gas atmosphere while depositing the anti-microbial metal. These atoms or molecules are incorporated in the coating either by being absorbed or trapped in the film, or by reacting with the metal being deposited. Both of these mechanisms during deposition are hereinafter referred to as "reactive depostion". Gases containing these elements, for example oxygen, hydrogen, and water vapour, may be provided continuously or may be pulsed for sequential deposition.

Anti-microbial composite materials are also preferably prepared by co- or sequentially depositing an anti-microbial metal with one or more inert biocompatible metals selected from Ta, Ti, Nb, Zn, V, Hf, Mo, Si, and Al. Alternatively, the composite materials may be formed by co-, sequentially or reactively depositing one or more of the anti-microbial metals as the oxides, carbides, nitrides, borides, sulphides or halides of these metals and/or the oxides, carbides, nitrides, borides, sulphides or halides of the inert metals. Particularly preferred composites contain oxides of silver and/or gold, alone or together with one or more oxides of Ta, Ti, Zn and Nb.

DESCRIPTION OF THE PREFERRED EMBODIMENTS

As above stated, the present invention has application beyond anti-microbial materials. However, the invention is disclosed herein with anti-microbial metals, which are illustrative of utility for other metals, metal alloys and metal compounds. Preferred metals include Al and Si, and the metal elements from the following groups of the periodic table: IIIB, IVB, VB, VIB, VIIB, VIIIEB, IB, IIB, IIIA, IVA, and VA (excluding As) in the periods 4, 5 and 6, (see Periodic Table as published in Merck Index 10th Ed., 1983, Merck and Co. Inc., Rahway, N. J., Martha Windholz). Different metals will have varying degrees of solubility. However, the creation and retention of atomic disorder in accordance with this invention results in enhanced solubility (release) of the metal as ions, atoms, molecules or clusters into an appropriate solvent i.e. a solvent for the particular material, typically a polar solvent, over the solubility of the material in its normal ordered crystalline state.

The medical devices formed from, incorporating, carrying or coated with the anti-microbial material of this invention generally come into contact with an alcohol or water based electrolyte including a body fluid (for example blood, urine or saliva) or body tissue (for example skin, muscle or bone) for any period of time such that microorganism growth on the device surface is possible. The term "alcohol or water based electrolyte" also includes alcohol or water based gels. In most cases the devices are medical devices such as catheters, implants, tracheal tubes, orthopaedic pins, insulin pumps, wound closures, drains, dressings, shunts, connectors, prosthetic devices, pacemaker leads, needles, surgical instruments, dental prostheses, ventilator tubes and the like. However, it should be understood that the invention is not limited to such devices and may extend to other devices useful in consumer healthcare, such as sterile packaging, clothing and footwear, personal hygiene products such as diapers and sanitary pads, in biomedical or biotechnical laboratory equipment, such as tables, enclosures and wall coverings, and the like. The term "medical device" as used herein and in the claims is intended to extend broadly to all such devices.

The device may be made of any suitable material, for example metals, including steel, aluminum and its alloys, latex, nylon, silicone, polyester, glass, ceramic, paper, cloth and other plastics and rubbers. For use as an in-dwelling medical device, the device will be made of a bioinert material. The device may take on any shape dictated by its utility, ranging from flat sheets to discs, rods and hollow tubes. The device may be rigid or flexible, a factor again dictated by its intended use.

Anti-Microbial Coatings

The anti-microbial coating in accordance with this invention is deposited as a thin metallic film on one or more surfaces of a medical device by vapour deposition techniques. Physical vapour techniques, which are well known in the art, all deposit the metal from the vapour, generally atom by atom, onto a substrate surface. The techniques include vacuum or arc evaporation, sputtering, magnetron sputtering and ion plating. The deposition is conducted in a manner to cream atomic disorder in the coating as defined hereinabove. Various conditions responsible for producing atomic disorder are useful. These conditions are generally avoided in thin film deposition techniques where the object is to cream a defect free, smooth and dense film (see for example J. A. Thornton, supra). While such conditions have been investigated in the art, they have not heretofore been linked to enhanced solubility of the coatings so-produced.

The preferred conditions which are used to create atomic disorder during the deposition process include:

- a low substrate temperature, that is maintaining the surface to be coated at a temperature such that the ratio of the substrate temperature to the melting point of the metal (in degrees Kelvin) is less than about 0.5, more preferably less than about 0.35 and most preferably less than about 0.3; and optionally one or both of:
- a higher than normal working (or ambient) gas pressure, i.e. for vacuum evaporation: e-beam or arc evaporation, greater than 0.01 mT, gas scattering evaporation (pressure plating) or reactive are evaporation, greater than 20 mT; for sputtering: greater than 75 mT; for magnetron sputtering: greater than about 10 mT; and for ion plating: greater than about 200 mT; and
- maintaining the angle of incidence of the coating flux on the surface to be coated at less than about 75°, and preferably less than about 30°

The metals used in the coating are those known to have an anti-microbial effect. For most medical devices, the metal must also be biocompatible. Preferred metals include the noble metals Ag, Au, Pt, Pd, and Ir as well as Sn, Cu, Sb, Bi, and Zn or alloys or compounds of these metals or other metals. Most preferred is Ag or Au, or alloys or compounds of one or more of these metals.

The coating is formed as a thin film on at least a part of the surface of the medical device. The film has a thickness no greater than that needed to provide release of metal ions on a sustainable basis over a suitable period of time. In that respect, the thickness will vary with the particular metal in the coating (which varies the solubility and abrasion resistance), and with the degree of atomic disorder in (and thus the solubility of) the coating. The thickness will be thin enough that the coating does not interfere with the dimensional tolerances or flexibility of the device for its intended utility. Typically, thicknesses of less than 1 micron have been found to provide sufficient sustained antimicrobial activity. Increased thicknesses may be used depending on the degree of metal ion release needed over a period of time. Thicknesses greater than 10 microns are more expensive to produce and normally should not be needed.

The anti-microbial effect of the coating is achieved when the device is brought into contact with an alcohol or a water based electrolyte such as, a body fluid or body tissue, thus releasing metal ions, atoms, molecules or clusters. The concentration of the metal which is needed to produce an anti-microbial effect will vary from metal to metal. Generally, anti-microbial effect is achieved in body fluids such as plasma, serum or urine at concentrations less than about 0.5–1.5 µg/ml.

The ability to achieve release of metal atoms, ions, molecules or clusters on a sustainable basis from a coating is dictated by a number of factors, including coating characteristics such as composition, structure, solubility and thickness, and the nature of the environment in which the device is used. As the level of atomic disorder is increased, the amount of metal ions released per unit time increases. For instance, a silver metal film deposited by magnetron sputtering at T/Tm<0.5 and a working gas pressure of about 7 mTorr releases approximately ⅓ of the silver ions that a film deposited under similar conditions, but at 30 mTorr, will release over 10 days. Films that are created with an intermediate structure (ex. lower pressure, lower angle of incidence etc.) have Ag release values intermediate to these values as determined by bioassays. This then provides a method for producing controlled release metallic coatings in accordance with this invention. Slow release coatings are prepared such that the degree of disorder is low while fast release coatings are prepared such that the degree of disorder is high.

For continuous, uniform coatings, the time required for total dissolution will be a function of film thickness and the nature of the environment to which they are exposed. The relationship in respect of thickness is approximately linear, i.e. a two fold increase in film thickness will result in about a two fold increase in longevity.

It is also possible to control the metal release from a coating by forming a thin film coating with a modulated structure. For instance, a coating deposited by magnetron sputtering such that the working gas pressure was low (ex. 15 mTorr) for 50% of the deposition time and high (ex. 30 mTorr) for the remaining time, has a rapid initial release of metal ions, followed by a longer period of slow release. This type of coating is extremely effective on devices such as urinary catheters for which an initial rapid release is required to achieve immediate anti-microbial concentrations followed by a lower release rate to sustain the concentration of metal ions over a period of weeks.

The substrate temperature used during vapour deposition should not be so low that annealing or recrystallization of the coating takes place as the coating warms to ambient temperatures or the temperatures at which it is to be used (ex. body temperature). This allowable ΔT, that the temperature differential between the substrate temperature during deposition and the ultimate temperature of use, will vary from metal to metal. For the most preferred metals of Ag and Au, preferred substrate temperatures of −20° to 200° C. more preferably −10° C. to 100° C. are used.

Atomic order may also be achieved, in accordance with the present invention, by preparing composite metal materials, that is materials which contain one or more anti-microbial metals in a metal matrix which includes atoms or molecules different from the anti-microbial metals.

Our technique for preparing composite material is to co- or sequentially deposit the anti-microbial metal(s) with one or more other inert, biocompatible metals selected from Ta, Ti, Nb, Zn, V, Hf, Mo, Si, Al and alloys of these metals or other metal elements, typically other transition metals. Such inert metals have a different atomic radii from that of the anti-microbial metals, which results in atomic disorder during deposition. Alloys of this kind can also serve to reduce atomic diffusion and thus stabilize the disordered structure. Thin film deposition equipment with multiple targets for the placement of each of the anti-microbial and inert metals is preferably utilized. When layers are sequentially deposited the layer(s) of the inert metal(s) should be discontinuous, for example as islands within the anti-microbial metal matrix. The final ratio of the anti-microbial metal(s) to inert metal(s) should be greater than about 0.2. The most preferable inert metals are Ti, Ta, Zn and Nb. It is also possible to form the anti-microbial coating from oxides, carbides, nitrides, sulphides, borides, halides or hydrides of one or more of the anti-microbial metals and/or one or more of the inert metals to achieve the desired atomic disorder.

Another composite material within the scope of the present invention is formed by reactively co- or sequentially depositing, by physical vapour techniques, a reacted material into the thin film of the anti-microbial metal(s). The reacted material is an oxide, nitride, carbide, boride, sulphide, hydride or halide of the anti-microbial and/or inert metal, formed in situ by injecting the appropriate reactants, or gases containing same, (ex. air, oxygen, water, nitrogen, hydrogen, boron, sulphur, halogens) into the deposition chamber. Atoms or molecules of these gases may also become absorbed or trapped in the metal film to create atomic disorder. The reactant may be continuously supplied during deposition for codeposition or it may be pulsed to provide for sequential deposition. The final ratio of anti-microbial metal(s) to reaction product should be greater than about 0.2. Air, oxygen, nitrogen and hydrogen are particularly preferred reactants.

The above deposition techniques to prepare composite coatings may be used with or without the conditions of lower substrate temperatures, high working gas pressures and low angles of incidence previously discussed. One or more of these conditions is preferred to retain and enhance the amount of atomic disorder created in the coating.

It may be advantageous, prior to depositing an anti-microbial in accordance with the present invention, to provide an adhesion layer on the device to be coated, as is known in the art. For instance, for a latex device, a layer of Ti, Ta or Nb may be first deposited to enhance adhesion of the subsequently deposited anti-microbial coating.

Anti-Microbial Powders

Anti-microbial powders, including nanocrystalline powders and powders made from rapidly solidified flakes or foils, can be formed with atomic disorder so as to enhance solubility. The powders either as pure metals, metal alloys or compounds such as metal oxides or metal salts, can be mechanically worked or compressed to impart atomic disorder. This mechanically imparted disorder is conducted under conditions of low temperature (i.e. temperatures less than the temperature of recrystallization of the material) to ensure that annealing or recrystallization does not take place. The temperature varies between metals and increases with alloy or impurity content.

Anti-microbial powders produced in accordance with this invention may be used in a variety of forms, for instance in topical creams, paints or adherent coatings. Alternatively, the powder may be incorporated into a polymeric, ceramic or metallic matrix to be used as a material for medical devices or coatings therefor.

The invention is further illustrated by the following non-limiting examples.

EXAMPLE 1

A medical suture material size 2/0, polyester braid was coated by magnetron sputtering an Ag-Cu-alloy onto the surface to a thickness of 0.45 microns, using either argon gas working pressures of 7 mTorr or 30 mT at 0.5 KW power and a T/Tm ratio of less than 0.5.

The anti-microbial effect of the coatings was tested by a zone of inhibition test. Basal medium Eagle (BME) with Earle's salts and L-glutamine was modified with calf/serum (10%) and 1.5% agar prior to being dispensed (15 ml) into Petri dishes. The agar containing Petri plates were allowed to surface dry prior to being inoculated with a lawn of *Staphylococcus aureus* ATCC#25923. The inoculant was prepared from Bactrol Discs (Difco, M.) which were reconstituted as per the manufacturer's directions. Immediately after inoculation, the materials or coatings to be tested were placed on the surface of the agar. The dishes were incubated for 24 h at 37° C. After this incubation period, the zone of inhibition was measured and a corrected zone of inhibition was calculated (corrected zone of inhibition=zone of inhibition−diameter of the test material in contact with the agar).

The results showed no zone of inhibition on the uncoated suture, a zone of less than 0.5 mm around the suture coated at 7 mTorr and a zone of 13 mm around the suture coated at 30 mTorr. Clearly the suture coated in accordance with the present invention exhibits a much more pronounced and effective anti-microbial effect.

EXAMPLE 2

This example is included to illustrate the surface structures which are obtained when silver metal is deposited on silicon wafers using a magnetron sputtering facility and different working gas pressures and angles of incidence (i.e. the angle between the path of the sputtered atoms and the substrate). All other conditions were as follows: deposition rate was 200 A°/min; ratio of temperature of substrate (wafer) to melting point of silver (1234° K.), T/Tm was less than 0.3. Argon gas pressures of 7 mTorr (a normal working pressure for metal coatings) and 30 mTorr were used. Angles of incidence at each of these pressures were 90° (normal incidence), 50° and 10°. The coatings had a thickness of about 0.5 microns.

The resulting surfaces were viewed by scanning electron microscope. As argon gas pressure increased from 7 to 30 mTorr the grain size decreased and void volume increased significantly. When the angle of incidence was decreased, the grain size decreased and the grain boundaries became more distinct. At 7 mTorr argon pressure and an angle of incidence of 10°, there were indications of some voids between the grains. The angle of incidence had a greater effect on the surface topography when the gas pressure was increased to 30 mTorr. At 90°, the grain size varied from 60–150 nm and many of the grains were separated by intergrain void spaces which were 15–30 nm wide. When the angle of incidence was decreased to 50°, the grain size decreased to 30–90 nm and the void volume increased substantially. At 10°, the grain size was reduced to about 10–60 nm and void volumes were increased again.

The observed nanometer scale changes in surface morphology and topography are indications of atomic disorder in the silver metal. While not being bound by the same, it is believed that such atomic disorder results in an increase in the chemical activity due to increased internal stresses and surface roughness created by mismatched atoms. It is believed that the increased chemical activity is responsible for the increased level of solubility of the coatings when in contact with an electrolyte such as body fluid.

The anti-microbial effect of the coatings was evaluated using the zone of inhibition test as set out in Example 1. Each coated silicon wafer was placed on an individual plate. The results were compared to the zones of inhibition achieved when solid silver (i.e. greater than 99% silver) sheets, wires or membranes were tested. The results are summarized in Table 1. It is evident that the pure silver devices and the silver sputtered coating at 7 mTorr do not produce any biological effect. However, the coatings deposited at a higher than normal working gas pressure, 30 mTorr, demonstrated an anti-microbial effect, as denoted by the substantial zones of inhibition around the discs. Decreasing the angle of incidence had the greatest effect on anti-microbial activity when combined with the higher gas pressures.

TABLE I

Antimicrobial effects of various silver and silver coated samples as determined using *Staphylococcus aureus*

| Sample | Percent Silver | Angle of Deposition | Working Gas Pressure (mTorr) | Corrected Zone of Inhibition (mm) |
|---|---|---|---|---|
| Silver Sheet-rolled | 99+ | — | — | <0.5 |
| Silver wire (.0045") | 99+ | — | — | <0.5 |
| Silver membrane-cast | 99+ | — | — | <0.5 |
| Sputtered thin film | 99+ | normal (90°) | 7 | <0.5 |
| Sputtered thin film | 99+ | 50° | 7 | <0.5 |
| Sputtered thin film | 99+ | 10° | 7 | <0.5 |
| Sputtered thin film | 99+ | normal (90°) | 30 | 6.3 |
| Sputtered thin film | 99+ | 50° | 30 | 10 |
| Sputtered thin film | 99+ | 10 | 30 | 10 |

EXAMPLE 3

Silicon wafers were coated by magnetron sputtering with an alloy of Ag and Cu (80:20) at normal incidence at working gas pressures of 7 mTorr and 30 mTorr, all other conditions being identical to those set out in Example 2. As in Example 2, when the coatings were viewed by SEM, the coatings formed at high working gas pressure had smaller grain sizes and larger void volumes than did the coatings formed at the lower working gas pressures.

Coatings which were similarly formed from a 50:50 Ag/Cu alloy were tested for anti-microbial activity with the zone of inhibition test set out in Example 1. The results are summarized in Table 2. Coatings deposited at low working gas pressure (7 mTorr) showed minimal zones of inhibition, while the coatings deposited at high working gas pressure (30 mTorr) produced larger zones of inhibition, indicative of anti-microbial activity.

TABLE 2

The antimicrobial effect of various sputter deposited silver-copper alloys as determined using *Staphylococcus aureus*

| Sample | Percent Silver | Angle of Deposition (°) | Working Gas Pressure (mTorr) | Corrected Zone of Inhibition (mm) |
|---|---|---|---|---|
| 1 | 50 | normal (90°) | 7.5 | <0.5 |
| 2 | 50 | normal (90°) | 30 | 16 |
| 3 | 50 | 10 | 30 | 19 |

EXAMPLE 4

A coating in accordance with the present invention was tested to determine the concentration of silver ions released into solution over time. One $cm^2$ silicon wafer discs were coated with silver as set forth in Example 2 at 7 mTorr and 30 mTorr and normal incidence to a thickness of 5000 A°. Using the method of Nickel et al., Eur. J. Clin. Microbiol., 4(2), 213–218, 1985, a sterile synthetic urine was prepared and dispensed into test tubes (3.5 ml). The coated discs were placed into each test tubes and incubated for various times at 37° C. After various periods of time, the discs were removed and the Ag content of the filtered synthetic urine was determined using neutron activation analysis.

The results are set forth in Table 3. The table shows the comparative amounts of Ag released over time from coatings deposited on discs at 7 mTorr or 30 mTorr. The coatings deposited at high pressure were more soluble than those deposited at low pressure. It should be noted that this test is a static test. Thus, silver levels build up over time, which would not be the case in body fluid where there is constant turn over.

TABLE 3

Concentration of silver in synthetic urine as a function of exposure time

| | Silver Concentration μg/ml | |
|---|---|---|
| Exposure Time (Days) | Working Argon gas pressure 7 mTorr | Working argon gas pressure 30 mTorr |
| 0 | ND1 | ND |
| 1 | 0.89 | 1.94 |
| 3 | 1.89 | 2.36 |
| 10 | 8.14 | 23.06 |

Note: Films were deposited at normal incidence (90°)
1-ND (non detectable) <0.46 μg/ml

EXAMPLE 5

This example is included to illustrate coatings in accordance with the present invention formed from another noble metal, Pd. The coatings were formed on silicon wafers as set forth in Example 2, to a thickness of 5000 A°, using 7 mTorr or 30 mTorr working gas pressures and angles of incidence of 90° and 10°. The coated discs were evaluated for antimicrobial activity by the zone of inhibition test substantially as set forth in Example 1. The coated discs were placed coating side up such that the agar formed a 1 mm surface coating over the discs. The medium was allowed to solidify and surface dry, after which the bacterial lawn was spread over the surface. The dishes were incubated at 37° C. for 24 h. The amount of growth was then visually analyzed.

The results are set forth in Table 4. At high working gas pressures, the biological activity of the coating was much greater than that of coatings deposited at low pressure. Changing the angle of incidence (decreasing) improved the anti-microbial effect of the coating to a greater extent when the gas pressure was low than when it was high.

TABLE 4

Surface Control of *Staphylococcus aureus* by Sputter Deposited Palladium metal

| Sample | Sputtering Pressure | Angle of Deposition | Antimicrobial Control |
|---|---|---|---|
| 1 | 7 mT | 90° (normal incidence) | More than 90% of surface covered by bacterial growth |
| 2 | 7 mT | 10° (grazing incidence) | 20–40% of surface covered by bacterial growth |
| 3 | 30 mT | 90° (normal incidence) | Less than 10% surface covered by bacterial growth |

EXAMPLE 6

This example is included to illustrate the effect of silver deposition temperature on the antimicrobial activity of the coating. Silver metal was deposited on 2.5 cm sections of a latex Foley catheter using a magnetron sputtering facility. Operating conditions were as follows; the deposition rate was 200 A° per minute; the argon working gas pressure was 30 mTorr; and the ratio of temperature of substrate to melting point of the coating metal silver, T/Tm was 0.30 or 0.38. In this example the angles of incidence were variable since the substrate was round and rough. That is the angles of incidence varied around the circumference and, on a finer scale, across the sides and tops of the numerous surface features. The antimicrobial effect was tested by a zone of inhibition test as outlined in Example 1.

The results showed corrected zones of inhibition of 0.5 and 16 mm around the tubing coated at T/Tm values of 0.38 and 0.30 respectively. The sections of Foley catheter coated at the lower T/Tm value were more efficacious than those coated at higher T/Tm value.

EXAMPLE 7

This example is included to demonstrate an antimicrobial coating formed by DC magnetron sputtering on a commercial catheter. A teflon coated latex Foley catheter was coated by DC magnetron sputtering 99.99% pure silver on the surface using the conditions listed in Table 5. The working gases used were commercial Ar and 99/1 wt % Ar/$O_2$.

The antimicrobial effect of the coating was tested by a zone of inhibition test. Mueller Hinton agar was dispensed into Petri dishes. The agar plates were allowed to surface dry prior to being inoculated with a lawn of *Staphylococcus aureus* ATCC#25923. The inoculant was prepared from Bactrol Discs (Difco, M.) which were reconstituted as per the manufacturer's directions. Immediately after inoculation, the coated materials to be tested were placed on the surface of the agar. The dishes were incubated for 24 hr. at 37° C. After this incubation period, the zone of inhibition was measured and a corrected zone of inhibition was calculated (corrected zone of inhibition=zone of inhibition–diameter of the test material in contact with the agar).

The results showed no zone of inhibition for the uncoated samples and a corrected zone of less than 1 mm for catheters sputtered in commercial argon at a working gas pressure of 5 mT. A corrected zone of inhibition of 11 mm was reported for the catheters sputtered in the 99/1 wt % Ar/$O_2$ using a working gas pressure of 40 mT. XRD analysis showed that the coating sputtered in 1% oxygen was a crystalline Ag film. This structure clearly caused an improved antimicrobial effect for the coated catheters.

TABLE 5

Conditions of DC Magnetron Sputtering Used for Anti-Microbial Coatings

| Samples Sputtered in Commercial Argon | Samples Sputtered in 99/1 wt % Ar/$O_2$ |
|---|---|
| Power 0.1 kW | Power 0.5 kW |
| Argon Pressure: 5 m Torr | Ar/$O_2$ Pressure: 40 mTorr |
| Initial Substrate Temperature: 20° C. | Initial Substrate Temperature: 20° C. |
| Cathode/Anode Distance: 40 mm | Cathode/Anode Distance: 100 mm |
| Film Thickness: 2500 A | Film Thickness: 3000 A |

EXAMPLE 8

This example demonstrates silver coatings formed by arc evaporation, gas scattering evaporation (pressure plating) and reactive arc evaporation. Evaporation of 99.99% silver was performed onto silicon or alumina wafers at an initial substrate temperature of about 21° C., using the parameters as follows:

Bias: −100 V

Current: 20 Amp-hrs

Angle of incidence: 90°

Working Gas Pressure: 0.01 mT (arc), 26 mT Ar/H$_2$ 96:4 (gas scattering evaporation), and 26 mT O$_2$ (reactive are evaporation)

No corrected ZOI was observed for wafers coated at vacuum (arc). Pressure plating with a working gas atmosphere containing Ar and 4% hydrogen produced a 6 mm ZOI, while a working gas atmosphere of pure oxygen (reactive arc) produced an 8 mm ZOI. Film thicknesses of about 4000 Angstroms were produced. The results indicate that the presence of gases such as hydrogen and/or oxygen in the arc evaporation atmosphere cause the coatings to have improved anti-microbial efficacy.

EXAMPLE 9

This example is included to illustrate composite materials to produce anti-microbial effects. A set of coatings were produced by RF magnetron sputtering zinc oxide onto silicon wafers as outlined below. The zinc oxide coatings showed no zone of inhibition.

Coatings of Ag and ZnO were deposited to a total thickness of 3300 Angstroms by sequentially sputtering layers of Ag with layers of ZnO, according to the conditions below, in a 75/25 wt % ratio. The coatings were demonstrated to have no zone of inhibition when the zinc oxide layers were about 100 Angstroms thick. However, films consisting of islands of very thin to discontinuous layers of ZnO (less than 50 Angstroms) in an Ag matrix (i.e. a composite film) had a 8 mm corrected zone of inhibition.

The conditions used to deposit ZnO were as follows: Working gas=argon; Working gas pressure=30 mT; Cathode-Anode distance: 40 mm; Initial Substrate Temperature: 21° C.; Power: RF magnetron, 0.5 kW.

The conditions used to deposit the Ag were as follows: Working gas=argon; Working gas pressure=30 mT; Cathode-Mode distance=40 mm; Initial Substrate Temperature=21° C.; Power=DC magnetron, 0.1 kW.

EXAMPLE 10

This example demonstrates the effects of cold working and annealing silver and gold powders on the antimicrobial efficacy demonstrated by a standard zone of inhibition test. Cold working of such powders results in a defective surface structure containing atomic disorder which favours the release of ions causing antimicrobial activity. The antimicrobial effect of this defective structure can be removed by annealing.

Nanocrystalline silver powder (crystal size about 30 nm) was sprinkled onto adhesive tape and tested. A zone of inhibition of 5 mm was obtained, using the method set forth in Example 7. A 0.3 g pellet of the nanocrystalline Ag powder was pressed at 40,000 psi. The pellet produced a 9 mm zone of inhibition when tested for antimicrobial activity. Nanocyrstalline silver powder was mechanically worked in a ball mill for 30 sec. The resulting powder was tested for antimicrobial activity, both by sprinkling the worked powder on adhesive tape and applying to the plates, and by pressing the powder into a pellet at the above conditions and placing the pellet on the plates. The zones of inhibition observed were 7 and 11 mm respectively. A pellet that had been pressed from the worked powder was annealed at 500° C. for 1 hour under vacuum conditions. A reduced zone of inhibition of 3 mm was observed for the annealed pellet.

These results demonstrate that nanocrystalline silver powder, while having a small anti-microbial effect on its own, has an improved antimicrobial effect by introducing atomic disorder by mechanical working of the powder in a ball mill or by pressing it into a pellet. The antimicrobial effect was significantly decreased by annealing at 500° C. Thus, conditions of mechanical working should not include or be followed by conditions such as high temperature, which allow diffusion. Cold mechanical working conditions are preferred to limit diffusion, for example by working at room temperature or by grinding or milling in liquid nitrogen.

Silver powder, 1 micron particle size, was tested in a manner similar to above. The Ag powder sprinkled onto adhesive tape and tested for a zone of inhibition. No zone of inhibition was observed. The powder was worked in a ball mill for 30 seconds and sprinkled onto adhesive tape. A 6 mm zone of inhibition was observed around the powder on the tape. When the Ag powder (as is or after mechanical working in the ball mill) was pressed into a 0.3 g pellet using 40,000 psi, zones of inhibition of 5 and 6 mm respectively were observed. A pellet which was formed from the ball milled powder and which was annealed at 500° C. for 1 hour had significantly reduced antimicrobial activity. Initially the pellet had some activity (4.5 mm zone of inhibition) but after the pellet was tested a second time, no zone of inhibition was observed. A control pellet which had not been annealed continued to give a zone of inhibition greater than 4 mm even after 14 repeats of the test. This demonstrates that an annealing step, following by mechanical working, limits the sustainable release of the antimicrobial silver species from the powders.

Nanocrystalline gold (20 nm crystals), supplied as a powder, was tested for anti-microbial effect by sprinkling the powder onto adhesive tape and using the zone of inhibition test. No zone of inhibition was recorded for the nanocrystalline gold powder. The gold powder was pressed into a 0.2 g pellet using 40,000 psi. A 10 mm zone of inhibition was observed. When the pressed pellets were subsequently vacuum annealed at 500° C. for 1 hour and the zone of inhibition was found to be 0 mm.

The results showed that solubility and thus the antimicrobial efficacy of gold powders can be improved by a mechanical working process such as pressing a nanocrystalline material into a pellet. The antimicrobial activity can be removed by annealing. Cold working is preferred.

Other gold powders including a 2–5 micron and a 250 micron particle size powder did not demonstrate an antimicrobial effect under the above mechanical working conditions. It is believed that the small grain size of the nanocrystalline gold powder was an important cofactor which, with the mechanical working, produced the desired antimicrobial effect.

EXAMPLE 11

This example is included to demonstrate a composite antimicrobial coating formed by reactive sputtering (another example of composite films). Example 7 demonstrates that an antimicrobial coating of silver can be obtained by sputtering in argon and 1% oxygen (0.5 kW, 40 mTorr, 100 mm anode/cathode distance, and 20° C.—produced a zone of inhibition of 11 mm).

When a working gas of argon and 20 wt % oxygen was used to sputter antimicrobial coatings under the conditions listed below in Table 6, the zones of inhibition ranged from 6 to 12 mm. This indicates that the provision of a reactive atmosphere during vapour deposition has the result of producing an antimicrobial film over a wide range of deposition process parameters.

TABLE 6

| Sputtering Conditions | |
|---|---|
| Target | 99.99% Ag |
| Working Gas: | 80/20 wt % Ar/O$_2$ |
| Working Gas Pressure: | 2.5 to 50 mTorr |
| Power | 0.1 to 2.5 kW |
| Substrate Temperature: | −5 to 20° C. |
| Anode/Cathode Distance | 40 to 100 mm |
| Base Pressure: | less than $4 \times 10^{-6}$ Torr |

EXAMPLE 12

This example demonstrates that the coatings of this invention have an antimicrobial effect against a broad spectrum of bacteria.

A total of 171 different bacterial samples encompassing 18 genera and 55 species were provide by the Provincial Laboratory of Public Health for Northern Alberta. These samples had been quick frozen in 20% skim milk and stored at −70° C. for periods ranging from several months to several years. Fastidious organisms which were unlikely to grow under conditions used in standard Kirby-Bauer susceptibility testing were not used.

Each frozen sample was scraped with a sterile cotton swab to inoculate a blood agar plate (BAP). The plates were incubated overnight at 35° C. The following morning isolated colonies were subcultured onto fresh BAPs and incubated at 35° C. overnight. The next day, the organisms were subjected to Kirby-Bauer susceptibility testing as described below.

Four to five colonies (more if colonies were small) of the same morphological type were selected from each BAP subculture and inoculated into individual tubes containing approximately 5 mL of tryptic soy broth (TSB). The broths were incubated at 35° C. for approximately 2 to 3 hours. At this time, the turbidity of most of the broth cultures either equalled or exceeded that of a 0.5 McFarland standard. The more turbid samples were diluted with sterile saline to obtain a turbidity visually comparable to that of the standard. To aid in the visual assessment of turbidity, tubes were read against a white background with contrasting black line.

A small number of the organisms (Streptococcus and Corynebacterium) did not grow well in TSB. The turbidity of these broths, after incubation, was less than that of the 0.5 McFarland standard. Additional colonies from the BAP subcultures were inoculated to these tubes to increase the turbidity to approximate that of the standard.

Within 15 minutes of adjusting the turbidity of the bacterial suspensions a sterile cotton swab was dipped into each broth. Excess fluid was removed by rotating the swab against the rim of the tube. The inoculum was applied to a Mueller Hinton (MH) agar plate by streaking the swab evenly in three directions over the entire agar surface. Three 1 cm×1 cm silver coated silica wafer squares were applied to each MH plate and the plates were inverted and incubated overnight at 35° C. The coatings had been sputtered under the following conditions, which through XFD analysis were shown to be silver/silver oxide composite films:

| | |
|---|---|
| Target: | 99.99% Ag |
| Working gas: | Ar/O$_2$ 80/20 |
| Working gas pressure: | 40 mT |
| Power: | 0.1 kW |
| Temperature of Deposition | 20° C. |
| Base pressure | $2 \times 10^{-6}$ Torr |
| Cathode/anode distance | 40 mm |

BAP cultures of control organisms were provided by the Provincial Laboratory and included: *Staphylococcus aureus* ATCC 25923; *Pseudomonas aeruginosa* ATCC 27853; *Escherichia coli:* ATCC 25922; and *Enterococcus faecalis* ATCC 29212 to check the quality of the MH agar. These cultures were treated in a like manner to the test organisms except that standard antibiotic discs rather than silver coated wafers were applied to the bacterial lawns on the MH agar. These organisms demonstrated that the MH agar was suitable for standard ZOI tests.

After 16 to 18 hours of incubation at 35° C. zones of inhibition around the silver wafers or antibiotic discs were measured to the nearest mm. Corrected zones were calculated by subtracting the size of the wafer (1 cm) from the size of the total zone. Representative zone of inhibition results are shown in Table 7.

TABLE 7

The Sensitivity of a Broad Range of Microorganisms to Silver* Coated Silicon Wafers

| Organism | Source | Corrected Zone of Inhibition (mm) |
|---|---|---|
| *Staphylococcus epidermidis* RC-455 | blood | 10 |
| *Bacillus licheniformis* R-2138 | tibia | 6 |
| *Corynebacterium* sp R-594 | leg | 10 |
| *Listeria monocytogenes* R-590 | blood | 5 |
| *Enterococcus faecalis* SR-113 | bone | 5 |
| *Streptococcus bovis* SR-62 | blood | 10 |
| *Escherichia coli* R-1878 | urine | 11 |
| *Klebsiella ozonae* R-308/90 | abdomen | 10 |
| *Enterobacter cloacae* R-1682 | unknown | 8 |
| *Proteus vulgaris* 3781 | urine | 4 |
| *Providencia stuartii* U-3179 | urine | 8 |
| *Citrobacter freundii* U-3122/90 | urine | 7 |
| *Salmonella typhimirium* ER-1154 | urine | 6 |
| *Serraria marcescens* R-850 | sputum | 6 |
| *Pseudomonas aeruginosa* U-3027 | urine | 10 |
| *Xanthomonas maltophila* 90-10B | unknown | 9 |
| *Aeromonas caviae* R-1211 | wound | 5 |
| *Branhamella catarrhalis* R-2681 | unknown | 12 |

Silver deposition*

EXAMPLE 13

This example demonstrates the use of tantalum as an adhesive layer for coatings of this invention. Tantalum is well known as a material which, in the form of an interlayer, improves adhesion of thin films to substrates. In this example test sections including a group of stainless steel (316) (1×1 cm) and silicon (1.7×0.9 cm) coupons and sections of latex tubing (5 cm) were cleaned in ethanol and then half of the test sections were coated (by sputtering) with a thin layer (approx. 100 Angstroms) of Ta before an antimicrobial silver film was deposited on them. The second group of the test sections were only coated with the antimicrobial Ag film. Coating conditions are listed below. While all test sections had similar antimicrobial activity, the Ta coated test sections had much better adhesion properties than did the untreated test sections. Adhesion properties were determined using ASTM method D3359-87, a standard test method for measuring adhesion.

| Sputtering Conditions | |
|---|---|
| Target: | 99.99% Ta |
| Working Gas: | 99/1 wt % Ar/$O_2$ |
| Working Gas Pressure: | 10 mTorr |
| Power: | 0.5 kW |
| Cathode/Anode Distance: | 100 mm |
| Substrate Temperature: | 20° C. |
| Target: | 99.99% Ag |
| Working Gas: | 99/1 wt % Ar/$O_2$ |
| Working Gas Pressure: | 40 mTorr |
| Power: | 0.5 kW |
| Cathode/Anode Distance: | 100 mm |
| Substrate Temperature: | 20° C. |

EXAMPLE 14

DC magnetron sputtering was used to deposit silver from a 99.98% pure cathode onto silicon and alumina wafers with commercial argon moisturized with water as the working gas. The argon was moisturized by passing it through two flasks containing 3 liters of room temperature water and one empty flask set up with glass wool to absorb any free liquid before the gas entered the sputtering unit.

The conditions of sputtering and the results of the standard zone of inhibition test performed on the sputtered silver films are shown below. Silver films which normally had no antimicrobial properties when deposited using argon that had not been treated with water yielded a corrected zone of inhibition of up to 8 mm when sputtered using a argon/water vapour mixture as the working gas.

TABLE 8

Conditions used for DC Magnetron Sputtering of Anti-Microbial Caotings

| Working Gas | Pressure | Power | Substrate Temperature | Anode/Cathode Distance | Corrected ZOI |
|---|---|---|---|---|---|
| Commercial Argon | 10 mTorr | 0.5 kW | −10° C. | 100 mm | 0 mm |
| Ar passed through $H_2O$ | 10 mTorr | 0.5 kW | −10° C. | 100 mm | 8 mm |

All publications mentioned in this specification are indicative of the level of skill of those skilled in the art to which this invention pertains. All publications are herein incorporated by reference to the same extent as if each individual publication was specifically and individually indicated to be incorporated by reference.

The terms and expressions in this specification are used as terms of description and not of limitation. There is no intention, in using such terms and expressions, of excluding equivalents of the features illustrated and described, it being recognized that the scope of the invention is defined and limited only by the claims which follow.

We claim:

1. A medical device intended for use in contact with an alcohol or water based electrolyte having an anti-microbial coating on its surface, comprising:

a medical device formed of a substantially bioinert structural material; and an anti-microbial coating formed on the surface of the medical device, said coating being formed from one or more anti-microbial metals and having sufficient atomic disorder such that the coating, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

2. The medical device as set forth in claim 1, wherein the deposition is performed by a physical vapour deposition technique selected from vacuum evaporation, sputtering, magnetron sputtering or ion plating.

3. The medical device as set forth in claim 2, wherein the metal is selected from the group consisting of Ag, Au, Pt, Pd, Ir, Sn, Cu, Sb, Bi, and Zn or alloys or compounds containing one or more of said metals.

4. The medical device as set forth in claim 2, wherein the metal is Ag, Au or Pd or an alloy or compound containing one or more of these metals.

5. The medical device as claimed in claim 1, wherein the coating is a composite coating formed from the anti-microbial metal in a matrix containing atoms or molecules of a material different from the anti-microbial metal, the atoms or molecules of the different material creating atomic disorder in the matrix.

6. The medical device as set forth in claim 5, wherein the different material is one or more of (a) reacted species of the anti-microbial metal or metal compound; (b) absorbed or trapped atoms or molecules of oxygen, nitrogen, hydrogen, boron, sulphur and halogen; and (c) an inert metal.

7. The medical device as set forth in claim 5, wherein the different material is one or more of (a) oxides, nitrides, hydrides, halides, borides, and carbides of an anti-microbial or an inert metal; and (b) absorbed or trapped atoms or molecules containing oxygen, nitrogen, hydrogen, boron, sulphur and halogen.

8. The medical device as claimed in claim 5, wherein the different material is an oxide, nitride, boride, sulphide, halide, or hydride of an inert metal selected from the group consisting of Ta, Ti, Nb, V, Hf, Zn, Mo, Si, and Al.

9. The medical device as claimed in claim 5, wherein the coating comprises silver oxide, silver metal, and optionally absorbed or trapped atoms or molecules containing oxygen, nitrogen, hydrogen, boron, sulphur, and halogen.

10. The medical device as claimed in claim 5, wherein the coating comprises silver oxide, silver oxide and optionally absorbed or trapped atoms or molecules containing oxygen.

11. The medical device as claimed in claim 1, wherein the anti-microbial metal is silver or an alloy or compound containing silver.

12. The medical device as claimed in claim 1, wherein the coating is formed by vapour deposition under conditions which limit diffusion during deposition and which limit annealing or recrystallization following deposition.

13. The medical device as claimed in claim 12, wherein the coating is formed by physical vapour deposition.

14. The medical device as claimed in claim 13, wherein the material is a coating of one or more anti-microbial metals formed on the medical device by vacuum evaporation, sputtering, magnetron sputtering or ion plating.

15. The medical device as claimed in claim 14, wherein the deposition is performed under conditions such that a ratio of the temperature of the medical device to the melting point of the metal or metal compound being deposited is maintained at less than about 0.5.

16. The medical device as claimed in claim 15, wherein the ratio is maintained at less than about 0.3.

17. The medical device as claimed in claim 15, wherein the deposition is performed such that an angle of incidence of the coating flux on the medical device to be coated is less than about 75°.

18. The medical device as claimed in claim 15, wherein the deposition is performed by arc evaporation at an ambient or working gas pressure of greater than about 0.01 mT.

19. The medical device as claimed in claim 15, wherein the deposition is performed by gas scattering evaporation at a working gas pressure of greater than about 20 mT.

20. The medical device as claimed in claim 15, wherein the deposition is performed by sputtering at a working gas pressure of greater than about 75 mT.

21. The medical device as claimed in claim 15, wherein the deposition is performed by magnetron sputtering at a working gas pressure of greater than about 10 mT.

22. The medical device as claimed in claim 15, wherein the deposition is performed by ion plating at a working gas pressure of greater than about 200 mT.

23. The medical device as set forth in claim 15, wherein the deposition is performed by magnetron sputtering at a working gas pressure of greater than about 30 mT.

24. A medical device intended for use in contact with an alcohol or water based electrolyte having an anti-microbial coating on its surface, comprising:
  a medical device formed of a substantially bioinert structural material; and
  an anti-microbial coating formed on the surface of the medical device, said coating being formed from one or more anti-microbial metals and having sufficient atomic disorder such that the coating, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis, the atomic disorder providing irregularities in surface topography and inhomogeneities in structure on a nanometer scale and being caused by high concentrations of one or more of point defects in a crystal lattice, vacancies, and line defects comprising dislocations, interstitial atoms, amorphous regions, grain and sub grain boundaries, relative to a normal ordered, crystalline state for the anti-microbial metal.

25. The medical device as set forth in claim 24, wherein the atomic disorder is created in the coating under conditions which limit diffusion such that sufficient atomic disorder is retained in the coating to provide release of atoms, ions, molecules or clusters of the anti-microbial metal into the alcohol or water based electrolyte at an enhanced rate relative to its normal ordered crystalline state.

* * * * *

UNITED STATES PATENT AND TRADEMARK OFFICE
CERTIFICATE OF CORRECTION

PATENT NO. : 5,681,575

DATED : October 28, 1997

INVENTOR(S) : Robert E. Burrell et al.

Page 1 of 2

It is certified that error appears in the above-identified patent and that said Letters Patent is hereby corrected as shown below:

| | | |
|---|---|---|
| In Col. 1, | Ln. 43, | change "In modem" to -- In modern --; |
| | Ln. 52, | change "have been make" to -- have been made --; |
| In Col. 3, | Ln. 10, | change "the thin rims" to -- the thin films --; |
| | Ln. 23, | change "The metal fill" to -- The metal film --; |
| In Col. 5, | Ln. 13, | change "less 75mT" to -- is less than 75mT --; |
| | Ln. 18, | change "reactive are" to -- reactive arc --; |
| | Ln. 46, | change "containing one more" to -- containing one or more --; |
| | Ln. 55, | change "from bull metals" to -- from bulk metals --; |
| In Col. 6, | Ln. 35, | change "with the fast metal" to -- with the first metal --; |
| In Col. 7, | Ln. 13, | change "VIIIEB" to -- VIIIB --; |
| | Ln. 64, | change "to cream atomic" to -- to create atomic --; |
| In Col. 8, | Ln. 1, | change "is to cream" to -- is to create --; |
| | Ln. 16, | change "reactive are" to -- reactive arc --; |
| In Col. 9, | Ln. 36, | change "Atomic order" to -- Atomic disorder --; |
| In Col. 12, | Ln. 5, | change "Staphylocococcus" to -- Staphylococcus--; |
| In Col. 15, | Ln. 7, | change "are evaporation" to -- arc evaporation --; |
| | Ln. 40, | change "Cathode-Mode" to -- Cathode-Anode --; |
| In Col. 16, | Ln. 30, | change "step,following by" to -- step, followed by --; |
| | Ln. 39, | change "When the pressed" to -- The pressed --; |

In Col. 19, please substitute the corrected Table 8, provided on the following page;

In Col. 20, Ln. 53, change "silver oxide, silver oxide" to -- silver oxide --.

UNITED STATES PATENT AND TRADEMARK OFFICE
CERTIFICATE OF CORRECTION

PATENT NO.   : 5,681,575
DATED        : October 28, 1997
INVENTOR(S)  : Robert E. Burrell et al.

It is certified that error appears in the above-identified patent and that said Letters Patent is hereby corrected as shown below:

Table 8: Conditions used for DC Magnetron Sputtering of Anti-Microbial Coatings

| Working Gas | Working Gas Pressure | Power | Substrate Temperature | Anode/Cathode Distance | Corrected ZOI |
|---|---|---|---|---|---|
| Commercial Argon | 10mTorr | 0.5kW | -10°C | 100 mm | 0 mm |
| Ar passed through $H_2O$ | 10mTorr | 0.5kW | -10°C | 100 mm | 8 mm |

Signed and Sealed this

Twenty-fourth Day of October, 2000

Attest:

Q. TODD DICKINSON

*Attesting Officer*  *Director of Patents and Trademarks*